(12) United States Patent
Nishiyama

(10) Patent No.: US 8,072,213 B2
(45) Date of Patent: Dec. 6, 2011

(54) NMR MEASUREMENT METHOD

(75) Inventor: Yusuke Nishiyama, Tokyo (JP)

(73) Assignee: JEOL Resonance Inc., Tokyo (JP)

( * ) Notice: Subject to any disclaimer, the term of this patent is extended or adjusted under 35 U.S.C. 154(b) by 320 days.

(21) Appl. No.: 12/561,484

(22) Filed: Sep. 17, 2009

(65) Prior Publication Data

US 2010/0072995 A1    Mar. 25, 2010

(30) Foreign Application Priority Data

Sep. 19, 2008  (JP) ................................ 2008-240398

(51) Int. Cl.
*G01V 3/00* (2006.01)

(52) U.S. Cl. ........................................ 324/309; 324/307

(58) Field of Classification Search .......... 324/300–322; 600/407–445
See application file for complete search history.

(56) References Cited

U.S. PATENT DOCUMENTS

| | | | |
|---|---|---|---|
| 6,794,866 B2 * | 9/2004 | Ferrage et al. ................ | 324/307 |
| 7,683,619 B2 * | 3/2010 | Smith et al. .................. | 324/309 |
| 7,894,891 B2 * | 2/2011 | Song et al. .................... | 600/546 |
| 2011/0105886 A1 * | 5/2011 | Song et al. .................... | 600/410 |

OTHER PUBLICATIONS

Stejskal et al., "Spin Diffusion Measurements: Spin Echoes in the Presence of a Time-Dependent Field Gradient," J. Chem. Physics, vol. 42, No. 1, Jan. 1, 1965, p. 288.

Earl et al., "Observations in Solid Polyethylenes by Carbon-13 Nuclear Magnetic Resonance With Magic Angle," Macromolecules, vol. 12, No. 4, Jul.-Aug. 1979, pp. 762-767.

Sullivan et al., "Spin Dynamics in the Carbon-13 Nuclear Magnetic Resonance Spectrometric Analysis of Coal by Cross Polarization and Magic-Angle Spinning," Anal. Chem., 1982.

Morris et al., "Diffusion-Ordered Two-Dimensional Nuclear Magnetic Resonance Spectroscopy," J. Am. Chem. Soc., 1992, vol. 114, pp. 3139-3141.

Schmidt-Rohr et al., Correlation of Structure, Mobility, and Morphological Information in Heterogeneous Polymer Materials by Two-Dimensional Wideline-Separation NMR.

Spectroscopy, Macromolecules, 1992, 25, pp. 3273-3277.

Morris et al., "Resolution of Discrete and Continuous Molecular Size Distributions by Means of Diffusion-Ordered 2D NMR Spectroscopy," J. Am. Chem. Soc., 1993,115, pp. 4291-4299.

* cited by examiner

*Primary Examiner* — Brij Shrivastav

(74) *Attorney, Agent, or Firm* — The Webb Law Firm

(57) ABSTRACT

An NMR measurement method adapted for measurements on solid mixture samples starts with irradiating a pulse sequence to the sample in order to measure the longitudinal magnetization relaxation times of nuclei possessing homogeneous longitudinal magnetization relaxation times (step 1). After a lapse of a given period of time t, a high-resolution NMR spectrum is acquired by nullifying spin diffusion across the nuclei (step 2). The steps 1 and 2 are repeated while varying the period of time t. The high-resolution NMR spectra are classified according to value of longitudinal magnetization relaxation time by inverse Laplace transform.

13 Claims, 13 Drawing Sheets

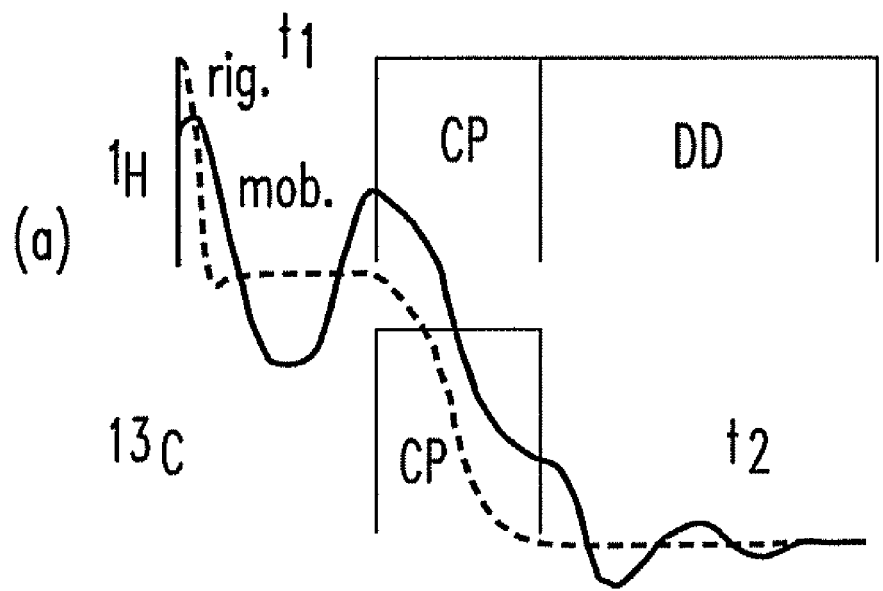
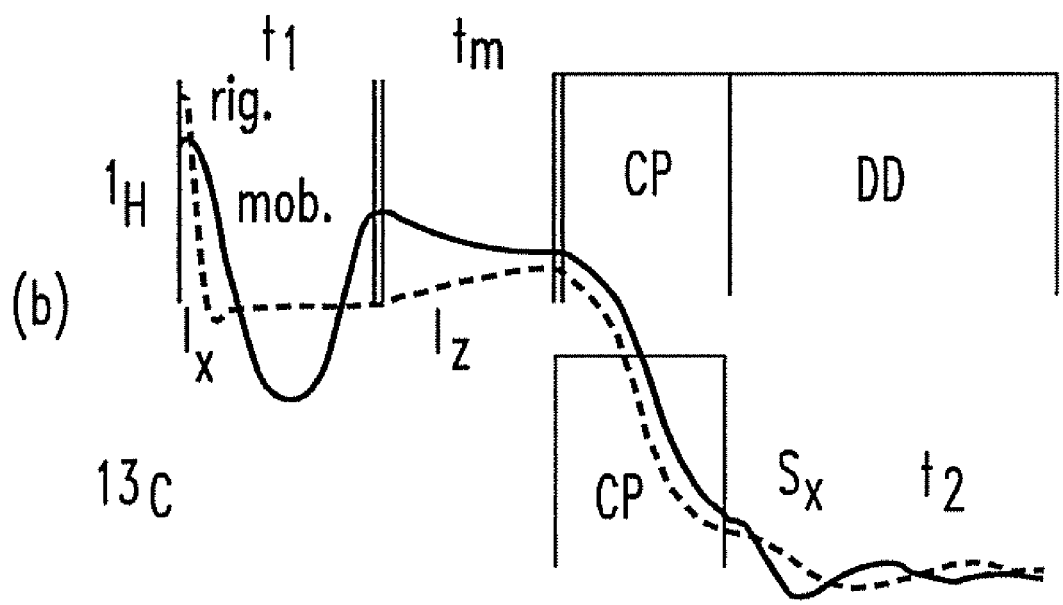
FIG. 6A

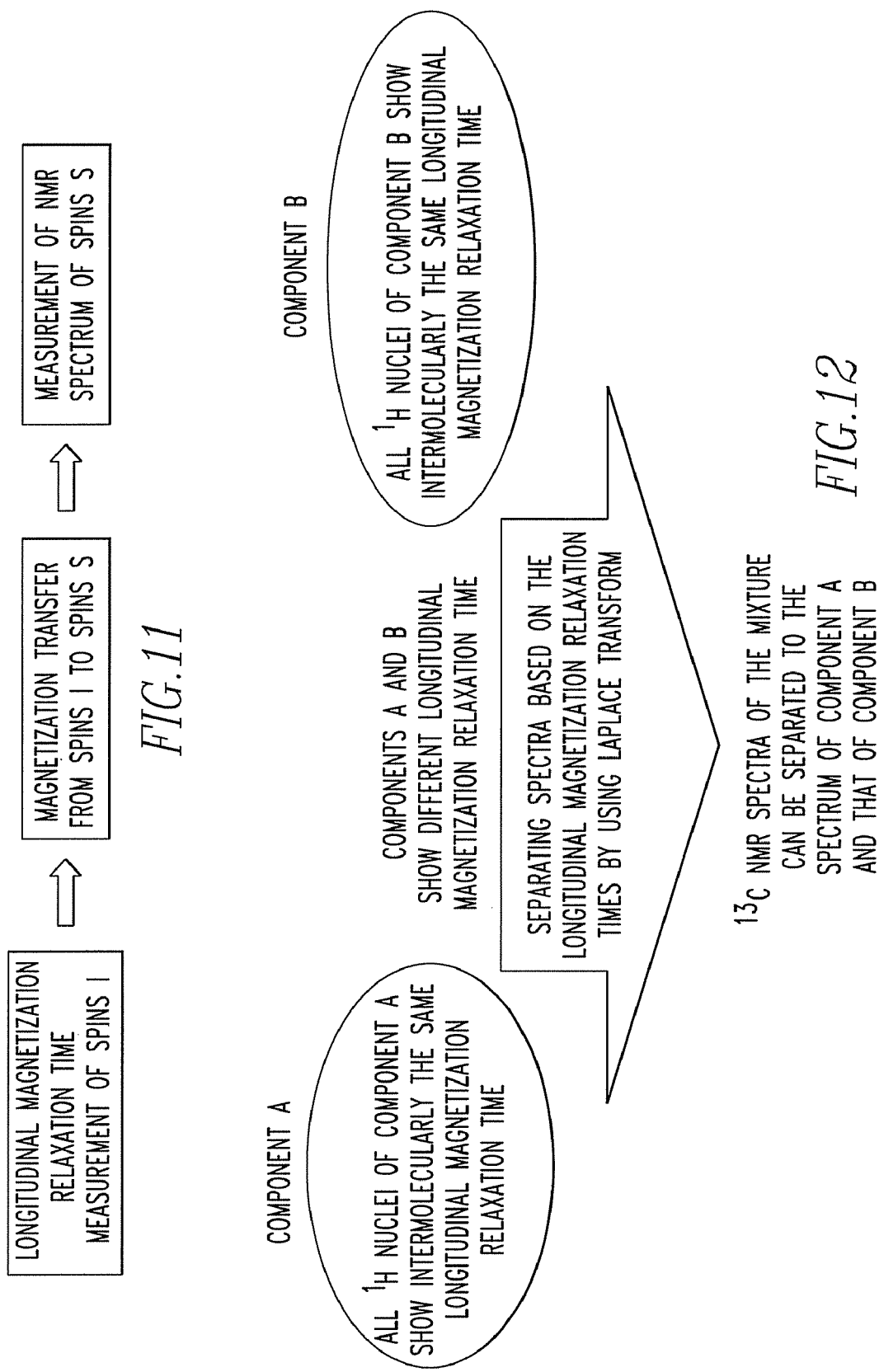

NMR MEASUREMENT METHOD

BACKGROUND OF THE INVENTION

1. Field of the Invention

The present invention relates to an NMR measurement method of investigating a sample having plural domains (such as a solid sample where plural components forming crystallites are mixed, a solid sample consisting of a single kind of molecules but having plural crystal systems intermingled, or a solid sample where crystal components and noncrystalline components are mixed) such that NMR spectra of the individual domains are respectively and separately acquired.

2. Description of Related Art

DOSY (diffusion-ordered spectroscopy) is now described as one example of an NMR measurement method for imaging individual components of a mixture respectively and separately and a method of using the inverse Laplace transform for analysis (see K. F. Morris, C. S. Johnson Jr., *Journal of American Chemical Society*, Vol. 114, p. 3139-3141 (1992) and K. F. Morris, C. S. Johnson Jr., *Journal of American Chemical Society*, Vol. 115, pp. 4291-4299 (1992)). DOSY is a method of NMR measurement that has become used in a wide range of fields as NMR instrumentation has been improved in accuracy and software programs for treating NMR data have been improved in recent years. DOSY is an expansion of NMR measurement originally proposed in 1965 by Stejskal and Tanner (E. O. Stejskal, J. E. Tanner, *Journal of Chemical Physics*, Vol. 42, No. 1, p. 288 (1965)).

If a sample that is a mixture of plural kinds of molecules is investigated by a DOSY experiment, NMR spectra of individual constituent molecules can be acquired respectively and separately by making use of differences in diffusion coefficient among the molecules.

Normally, an NMR spectrum of a mixture is observed as a superimposition of spectral components of individual sample components as shown in FIG. 1. On the other hand, each molecular species has an intrinsic value of molecular diffusion coefficient. Therefore, if NMR peaks in an NMR spectrum of a mixture are classified by molecular diffusion coefficient, then NMR spectra of individual molecular species can be acquired respectively and separately.

Diffusion coefficients are measured by observing NMR spectra plural times while varying the diffusion measurement time. In a normal method of DOSY, as the diffusion measurement time or the diffusion rate is increased, the signal intensity of the NMR spectrum attenuates to a greater extent as shown in FIG. 2. Therefore, the signal intensity of an NMR spectrum attenuates at a higher rate with an increasing diffusion rate in a given diffusion measurement time, and vice versa.

The diffusion coefficient is found by analyzing the decay curve. NMR spectra are separated according to diffusion coefficient using inverse Laplace transform. Sharp peaks appear at the positions of the values of diffusion coefficients by using inverse Laplace transform. This facilitates analyzing the spectrum. FIG. 3 shows an example of the result obtained by performing inverse Laplace transform while taking notice of one peak intensity.

Peaks having signal intensities which are made to show identical attenuation behaviors by diffusion are classified into groups by inverse Laplace transform. The result is shown in FIG. 4, where the spectrum can be separated into a spectral component group of slow diffusion A and a spectral component group of fast diffusion B.

In a DOSY method, spectral components are separated according to diffusion coefficient using inverse Laplace transform. As a result, the spectral components can be separated according to component and observed. This is a method of separation employing the fact that each molecule has an intrinsic value of diffusion coefficient.

Measurement methods of separating plural spectral components by making use of differences in relaxation time are also known besides DOSY. Three of them are next introduced.

(1) A measurement method of separating plural spectral components by making use of differences in longitudinal magnetization relaxation time of $^{13}C$ (carbon) nuclei.

This is a method of separating NMR signals using differences in longitudinal magnetization relaxation time of $^{13}C$ nuclei as indices. When a $^{13}C$ NMR spectrum is observed while varying the relaxation measurement time, signal intensity variations reflect relaxation time variations.

Data obtained by actual measurements on polyethylene is shown in FIG. 5 (quoted from W. L. Earl and D. L. Vander Hart, *Macromolecules*, Vol. 12, pp. 762-767 (1979)). In the measurements, an inversion recovery method was used. That is, the longitudinal magnetization relaxation time of each $^{13}C$ carbon nucleus was measured by measuring the time in which an inverted signal recovered. The caption for FIG. 5 reads: "$^{13}C$ spectra at 30° C. displaying the rapid recovery of the noncrystalline component (NCC) resonance centered at 31.7 ppm. The pulse sequence on the carbons is $(180°-90°-10 \text{ s})_{\tau}$; values of $\tau$ are indicated. The protons are continuously irradiated at a low level producing Overhaused (OV) enhancement of the carbon signals to avoid transient Overhauser effects. The weaker crystalline resonance at 34.1 ppm is much attenuated in all of these spectra due to a very long $T_{1C}$. The $T_{1C}$ of the NCC carbons is 175±25 ms."

When the relaxation measurement time ($\tau$) was 0.025 s, both of signal of 35 ppm and signal of 31 ppm were inverted. When the relaxation measurement time was then set to 10 s, both signals had positive intensities but their behaviors during this time interval were different.

Although the signal of 31 ppm recovered to a positive intensity in the relaxation measurement time of 0.1 s, the signal of 35 ppm did not recover to a positive intensity until the relaxation measurement time of 1 s. Through this sequence of measurements, the signal of 31 ppm and the signal of 35 ppm can be classified as signals having different relaxation times.

The longitudinal magnetization relaxation times of $^{13}C$ nuclei are affected more strongly by local modes of motion of molecules. Consequently, it can be said that separation of signals using longitudinal magnetization relaxation times of $^{13}C$ nuclei is a separation method in which local differences in motion of molecules are reflected.

(2) A measurement method of separating signals by making use of differences in transverse magnetization relaxation time among $^1H$ (hydrogen) nuclei and magnetization transfer from $^1H$ nuclei to $^{13}C$ nuclei.

In this method, the spectrum is observed while varying the measurement time of the transverse magnetization relaxation time. Prior to the observation, magnetization transfer is done from $^1H$ nuclei to $^{13}C$ nuclei. The spectrum is observed with the $^{13}C$ carbon nuclei. In a $^1H$ NMR spectrum, peaks of broad linewidths overlap with each other and are not separated well. On the other hand, in a $^{13}C$ NMR spectrum, peaks have narrow linewidths and so various peaks can be separated and observed.

Accordingly, magnetization transfer from $^1H$ nuclei to $^{13}C$ nuclei and subsequent peak observation at $^{13}C$ nuclei are useful for peak separation. Data about the transverse magnetization relaxation time of $^1$H nuclei is derived by performing Fourier transform and obtaining a spectrum.

By performing Fourier transform, fast components of the transverse magnetization relaxation appear as peaks of broad linewidths, while slow components appear as peaks of narrow linewidths. The processing consisting of Fourier-transforming time-domain signals and displaying the result as a spectrum follows the conventional procedure of NMR. This processing does not improve signal separation.

FIG. 6A shows a schematic representation of this method of measurement (a) and data obtained by actual measurement (b). Both are taken from the Stejskal and Tanner article. In (a), portion "CP" indicates magnetization transfer. It can be seen from (b) that three peaks are separated and observed in the direction of $^{13}$C axis. The caption for FIG. 6A reads: "FIG. 1. Pulse sequence and principle of the heteronuclear 2D WISE-NMR experiment. (a) Basic version with proton evolution, cross polarization (CP), and $^{13}$C detection with dipolar decoupling of protons (DD). Typical magnetization decays are sketched. For simplicity, just two components, a 'rigid' and a 'mobile' one, are considered. At the start of the detection period, the four 180° pulses of the TOSS sequence (not shown here) can be applied to suppress $^{13}$C spinning sidebands. (b) Extension by a mixing time before cross polarization. The decrease of the difference between proton magnetization levels by proton spin diffusion during the mixing time is indicated." The caption for FIG. 6B reads: "FIG. 2. WISE-NMR spectra of PS-b-PDMS (50:50 mol %) for a series of mixing times. (a) Minimum effective $t_m$ of 0.5 ms, due to the CP contact time of 1 ms. The PDMS (line near 0 ppm) is highly mobile but does not induce significant mobility in the PS (lines at 40, 127, and 144 ppm; the $^1$H line width averaged between phenyl and methylene protons is 40 kHz). (b) $t_m$=20 ms. The PDMS within 1 nm from the PS-PDMS interface is detected in the sharp components on the PS signals. (c) Within a mixing time of $t_m$=200 ms, the $^1$H magnetization is approaching spatial equilibration."

The peak separation has been accomplished by magnetization transfer from $^1$H nuclei to $^{13}$C nuclei and observation of an NMR spectrum at $^{13}$C nuclei. On the other hand, a spectral peak indicated by PDMS in the direction of $^1$H axis is very narrow, whereas a spectral peak indicated by PS is broad. In this way, peaks can be classified by their linewidth on the $^1$H axis side.

The transverse magnetization relaxation times of $^1$H nuclei are affected strongly by local modes of motion of molecules, in the same way as the longitudinal magnetization relaxation times of $^{13}$C nuclei. Therefore, it can be said that signal separation relying on transverse magnetization relaxation times of $^1$H nuclei reflects the differences in local kinetics of molecules.

(3) A method of measuring the longitudinal magnetization relaxation times of $^1$H nuclei as an NMR spectrum of $^{13}$C nuclei by performing magnetization transfer to $^{13}$C nuclei.

This method consists of observing the longitudinal magnetization relaxation times of $^1$H nuclei, then performing magnetization transfer from $^1$H nuclei to $^{13}$C nuclei, and acquiring an NMR spectrum of $^{13}$C nuclei as shown in FIG. 7. The results of measurement of the longitudinal magnetization relaxation times of $^1$H nuclei appear as variations in intensity of a $^{13}$C NMR spectrum (M. J. Sullivan and G. E. Maciel, *Anal. Chem.*, Vol. 54, pp. 1615-1623 (1982).

The longitudinal magnetization relaxation times of $^1$H nuclei are uniform within each individual molecule due to $^1$H-$^1$H homonuclear spin diffusion. This fact and the measurement methods (1)-(3) above are summarized in detail in K. Schmidt-Rohr and H. W. Spiess in "Multidimensional solid state NMR and polymers," Academic Press (1994).

When NMR spectra of solution samples consisting of mixtures are acquired, DOSY is most frequently used as mentioned previously because NMR spectra can be separated according to each sample component by the use of DOSY. In DOSY, spectra are separated by employing differences in translational diffusion coefficient among molecules in a solution. However, no translational diffusion occurs in solid samples. Therefore, there is the problem that DOSY cannot be applied to solid samples.

On the other hand, if the method (1) above is used, signals originating from a mixture sample can be separated by making use of differences in longitudinal magnetization relaxation time among $^{13}$C nuclei. However, the longitudinal magnetization relaxation times of $^{13}$C nuclei reflect local kinetics of molecules and so the separation using this measurement method depends on differences among local kinetics of molecules. Consequently, NMR peaks are not always classified according to molecular species.

In particular, in a case where molecules contain methyl groups, there is the problem that peaks of the methyl groups and other peaks of the same molecule are observed to be separated because the methyl groups show very high mobility.

If the above-described method (2) is used, NMR peaks of a mixture sample can be separated by making use of differences in transverse magnetization relaxation time among $^1$H nuclei. This method also depends on differences in local kinetics of molecules in the same way as peak separation relying on the longitudinal magnetization relaxation times of $^{13}$C nuclei. Consequently, NMR peaks are not always separated according to molecular species.

In particular, in a case where molecules contain methyl groups, there is the problem that peaks of the methyl groups and other peaks of the same molecule are observed to be separated because the methyl groups show very high mobility.

If the above-described method (3) is used, experiments of measurements of the longitudinal magnetization relaxations of $^1$H nuclei and experiments of magnetization transfer from $^1$H nuclei to $^{13}$C nuclei show that the longitudinal magnetization relaxation times of $^1$H nuclei can be derived as variations in $^{13}$C NMR signal intensity of molecules to which $^1$H nuclei belong. Normally, this method of measurement is applied only to samples of pure substances. If this method of measurement can be applied to mixture samples, great advantages will be obtained. But this method requires tedious analysis of $^{13}$C signal variation.

When spins I (normally, $^1$H (hydrogen) nuclei) have a uniform longitudinal magnetization relaxation time within each molecule due to spin diffusion, if spectral peaks of the spins I can be classified by longitudinal magnetization relaxation time of the spins I, the spectral peaks of the spins I can be separated according to molecular species.

However, the spectral peaks of the spins I are broadened and made featureless due to spin diffusion. Therefore, it is difficult to separate the spectral peaks of the spins I according to longitudinal magnetization relaxation time of the spins I.

If the peaks can be separated, the obtained spectrum is a featureless spectrum of the spins I having broad peaks. The spectrum has a small amount of information. In order to derive a spectrum having a large amount of information, it is essential to acquire a high-resolution spectrum.

SUMMARY OF THE INVENTION

In view of the foregoing, it is an object of the present invention to provide an NMR measurement method adapted to measure a solid sample consisting of a mixture sample. In particular, the method makes it possible to separate NMR spectra according to molecular species by a relatively simple method, based on differences in longitudinal relaxation time among spins I (normally, 1H (hydrogen) nuclei), the spectra being derived either from the spins I or from spins S (normally, $^{13}$C (carbon) nuclei) coupled to the spins I.

To achieve this object, the present invention provides an NMR measurement method for obtaining NMR spectra, respectively, of plural components of a sample when the components have a uniform longitudinal magnetization relaxation time in each individual domain of the sample due to spin diffusion. The method starts with irradiating the sample with a pulse sequence for measuring the above-described uniform longitudinal magnetization relaxation time of nuclei (first step). After a lapse of a given period of time t, the spin diffusion of the nuclei having the uniform magnetization relaxation time is nullified, and a high-resolution NMR spectrum is acquired (step 2). The steps 1 and 2 are repeated while varying the period of time t to obtain plural high-resolution NMR spectra. The high-resolution NMR spectra are classified according to value of longitudinal magnetization relaxation time by inverse Laplace transform, based on differences in recovery or decay rate of NMR signal intensity that recovers or decays dependently on longitudinal magnetization relaxation time.

In one feature of the NMR measurement method, the measurement of the longitudinal magnetization relaxation time is measurement of longitudinal magnetization relaxation time by making use of an inversion recovery method, or saturation recovery method, and measurement of longitudinal magnetization relaxation time in a rotating frame by making use of a spin locking method.

The nullification of the spin diffusion is achieved by RF irradiation for nullifying homonuclear interactions or high-speed rotation of the sample or by both.

In another feature of the NMR measurement method, the nuclei having the uniform longitudinal magnetization relaxation time are $^1$H nuclei or $^{19}$F nuclei.

The present invention also provides an NMR measurement method for obtaining NMR spectra, respectively, of plural components of a sample when the components have a uniform longitudinal magnetization relaxation time in each individual domain of the sample due to spin diffusion. The method starts with irradiating the sample with a pulse sequence for measuring the above-described uniform longitudinal magnetization relaxation time of first nuclei (step 1). After a lapse of a given period of time t, transfer of magnetization is made to the second nuclei from which excitation energies for the first nuclei can be acquired as a high-resolution NMR spectrum of the second nuclei (step 2). The steps 1 and 2 are repeated while varying the period of time t to acquire plural high-resolution NMR spectra of the second nuclei. The high-resolution NMR spectra of the second nuclei are classified according to value of longitudinal magnetization relaxation time by inverse Laplace transform, based on differences in recovery or decay rate of NMR signal intensity that recovers or decays dependently on longitudinal magnetization relaxation time.

In one feature of this NMR measurement method, the measurement of the longitudinal magnetization relaxation time is measurement of longitudinal magnetization relaxation time by making use of an inversion recovery method or saturation recovery method, and measurement of longitudinal relaxation time in a rotating frame by making use of the spin locking method.

In another feature of this NMR measurement method, the first nuclei are $^1$H nuclei or $^{19}$F nuclei.

In a further feature of this NMR measurement method, the second nuclei are other than $^1$H nuclei and can give rise to high-resolution NMR spectra.

In yet another feature of this NMR measurement method, the second nuclei are $^{13}$C nuclei, $^{15}$N nuclei, $^{29}$Si nuclei, or $^{31}$P nuclei.

One embodiment of the present invention provides an NMR measurement method for obtaining NMR spectra, respectively, of plural components of a sample when the components have a uniform longitudinal magnetization relaxation time in each individual domain of the sample due to spin diffusion. The method starts with irradiating the sample with a pulse sequence for measuring the above-described uniform longitudinal magnetization relaxation time of nuclei (step 1). After a lapse of a given period of time t, the spin diffusion of the nuclei having the uniform magnetization relaxation time is nullified to acquire a high-resolution NMR spectrum (step 2). The steps 1 and 2 are repeated while varying the period of time t to obtain plural high-resolution NMR spectra. The high-resolution NMR spectra are classified according to value of longitudinal magnetization relaxation time by inverse Laplace transform, based on differences in recovery or decay rate of NMR signal intensity that recovers or decays dependently on longitudinal magnetization relaxation time. Consequently, an NMR measurement method can be offered which is adapted to investigate a solid sample by separating NMR spectra originating from spins I according to molecular species, based on differences in longitudinal relaxation time among spins I (normally, $^1$H nuclei), by a relatively simple method.

Another embodiment of the present invention provides an NMR measurement method for obtaining NMR spectra, respectively, of plural components of a sample when the components have a uniform longitudinal magnetization relaxation time in each individual domain of the sample due to spin diffusion. The method starts with irradiating the sample with a pulse sequence for measuring the above-described uniform longitudinal magnetization relaxation time of first nuclei (step 1). After a lapse of a given period of time t, transfer of magnetization is made to a second nuclei from which excitation energies for the first nuclei can be acquired as a high-resolution NMR spectrum of the second nuclei (step 2). The steps 1 and 2 are repeated while varying the period of time t to acquire plural high-resolution NMR spectra of the second nuclei. The high-resolution NMR spectra of the second nuclei are classified according to the value of longitudinal magnetization relaxation time by inverse Laplace transform, based on differences in recovery or decay rate of NMR signal intensity that recovers or decays dependently on longitudinal magnetization relaxation time.

Consequently, an NMR measurement method can be offered which is adapted to investigate a solid sample by separating NMR spectra originating from spins S (normally, $^{13}$C nuclei) coupled to spins I (normally, $^1$H nuclei) according to molecular species, based on differences in longitudinal relaxation time among the spins I, by a relatively simple method.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

FIG. 11 is a chart illustrating another example of an NMR measurement method associated with the present invention;

FIG. 12 is a chart illustrating a further example of an NMR measurement method associated with the present invention;

DESCRIPTION OF THE PREFERRED EMBODIMENTS

The preferred embodiments of the present invention are hereinafter described with reference to the accompanying drawings. In the present invention, high-resolution NMR spectra are classified based on longitudinal magnetization relaxation times of spin I (normally, $^{1}H$ (hydrogen) nuclei). With respect to the longitudinal magnetization relaxation times of the spins I, it is assumed that the relaxation time is uniform within each domain of a sample made of the same component even in a multicomponent mixture.

That is, in each domain of a sample made of the same component, $^{1}H$ nuclei have a uniform longitudinal magnetization relaxation time $T_1$ due to spin diffusion. However, spin diffusion does not take place across domains made of different components. Therefore, $^{1}H$ nuclei possess different values of longitudinal magnetization relaxation time $T_1$ for each different component (for each different domain).

A system having particles (domains) having such a uniform longitudinal magnetization relaxation time is realized by homonuclear spin diffusion when a single kind of nuclear atoms having nuclear spins are present at high density. An NMR spectrum produced from this system has peaks that are broadened and made featureless due to spin diffusion.

In the present invention, relaxation times are measured under the condition where each component of the sample produces spectral components having uniform longitudinal magnetization relaxation time due to spin diffusion. Consequently, NMR spectral components arising from a mixture consisting of plural components are classified according to each component using the longitudinal magnetization relaxation times as indices. The classification is performed using inverse Laplace transform. As a result, sharpened NMR peaks show up in the spectrum.

The aforementioned object of the present invention is achieved by suppressing the spin diffusion among nuclear spins to obtain a high-resolution NMR spectrum or by shifting magnetization to nuclei from which a high-resolution NMR spectrum can be acquired to obtain a high-resolution NMR spectrum.

Embodiment 1

Figure 1:
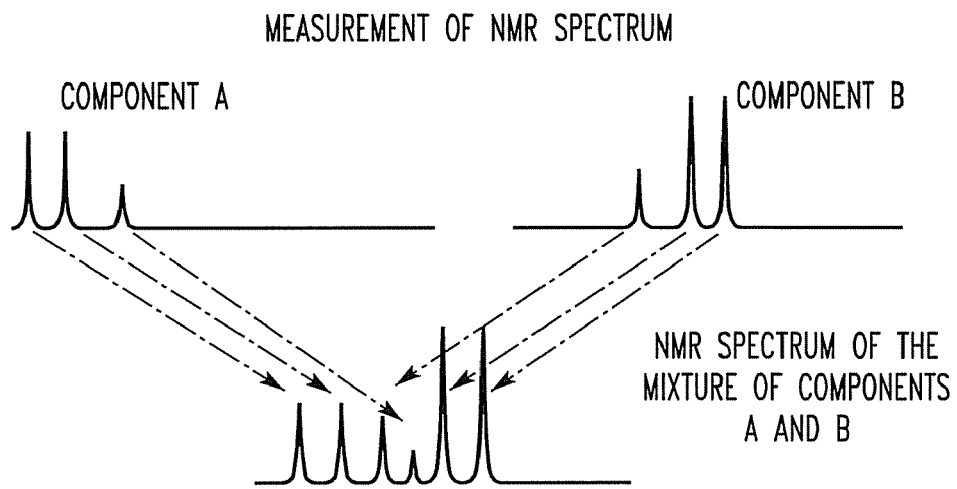
FIG. 1 is a schematic chart showing an NMR spectrum of a mixture sample.
Figure 2:
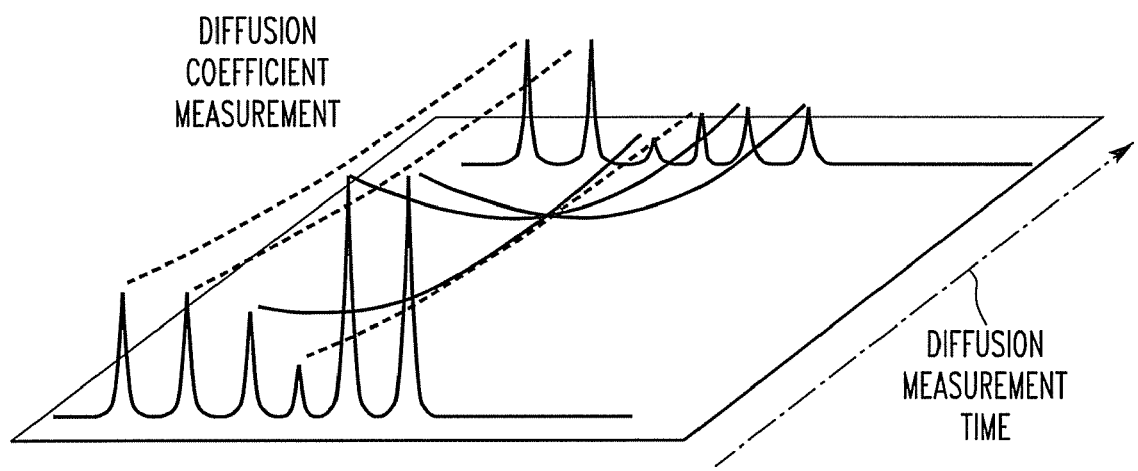
FIG. 2 is a schematic chart illustrating measurement of the longitudinal magnetization relaxation times of the mixture sample.
Figure 3:
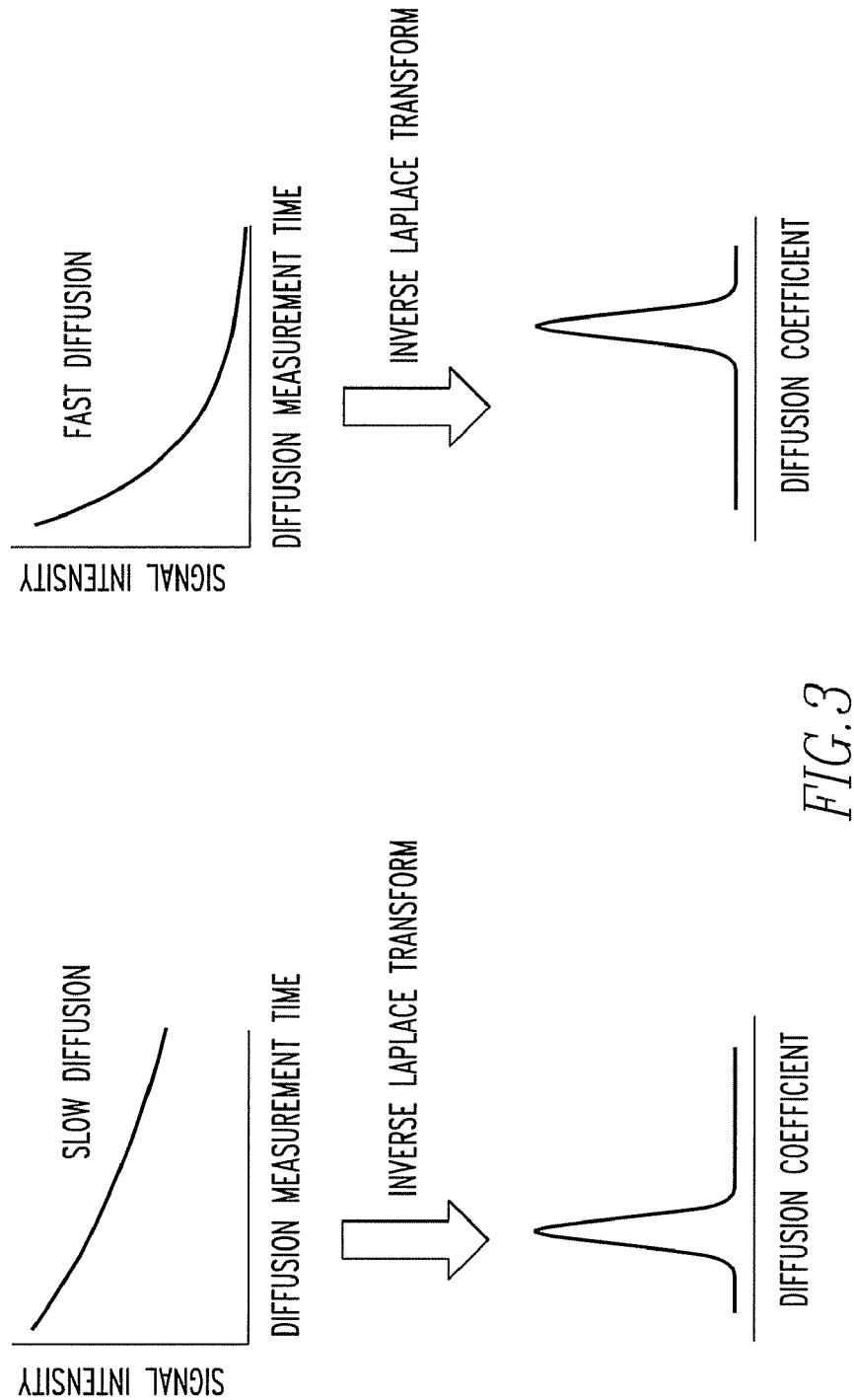
FIG. 3 schematically illustrates the concept of inverse Laplace transform.
Figure 4:
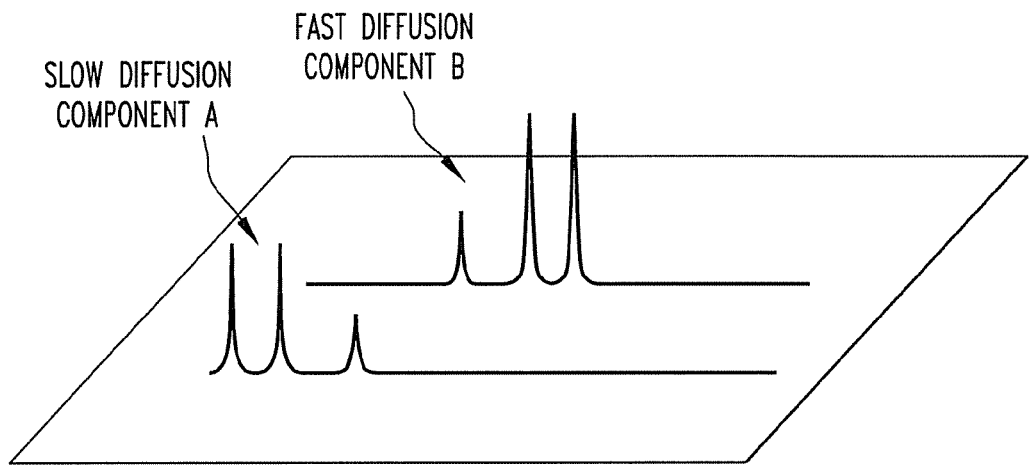
FIG. 4 is a schematic chart illustrating how peaks in an NMR spectrum are separated by inverse Laplace transform.
Figure 5:
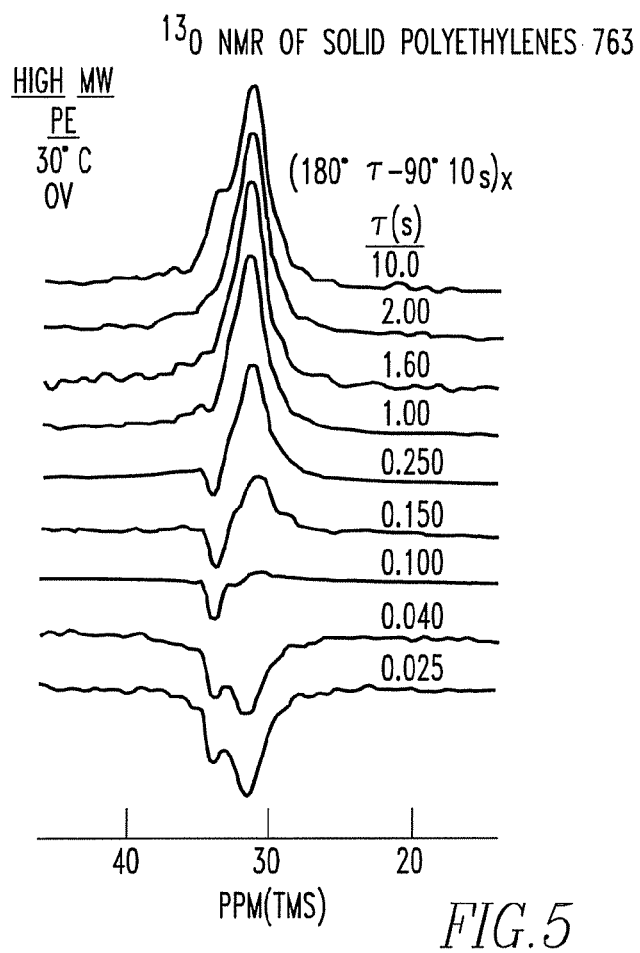
FIG. 5 is a chart illustrating the results of measurement of longitudinal magnetization relaxation times of $^{13}C$ nuclei of polyethylene.
Figure 6B:
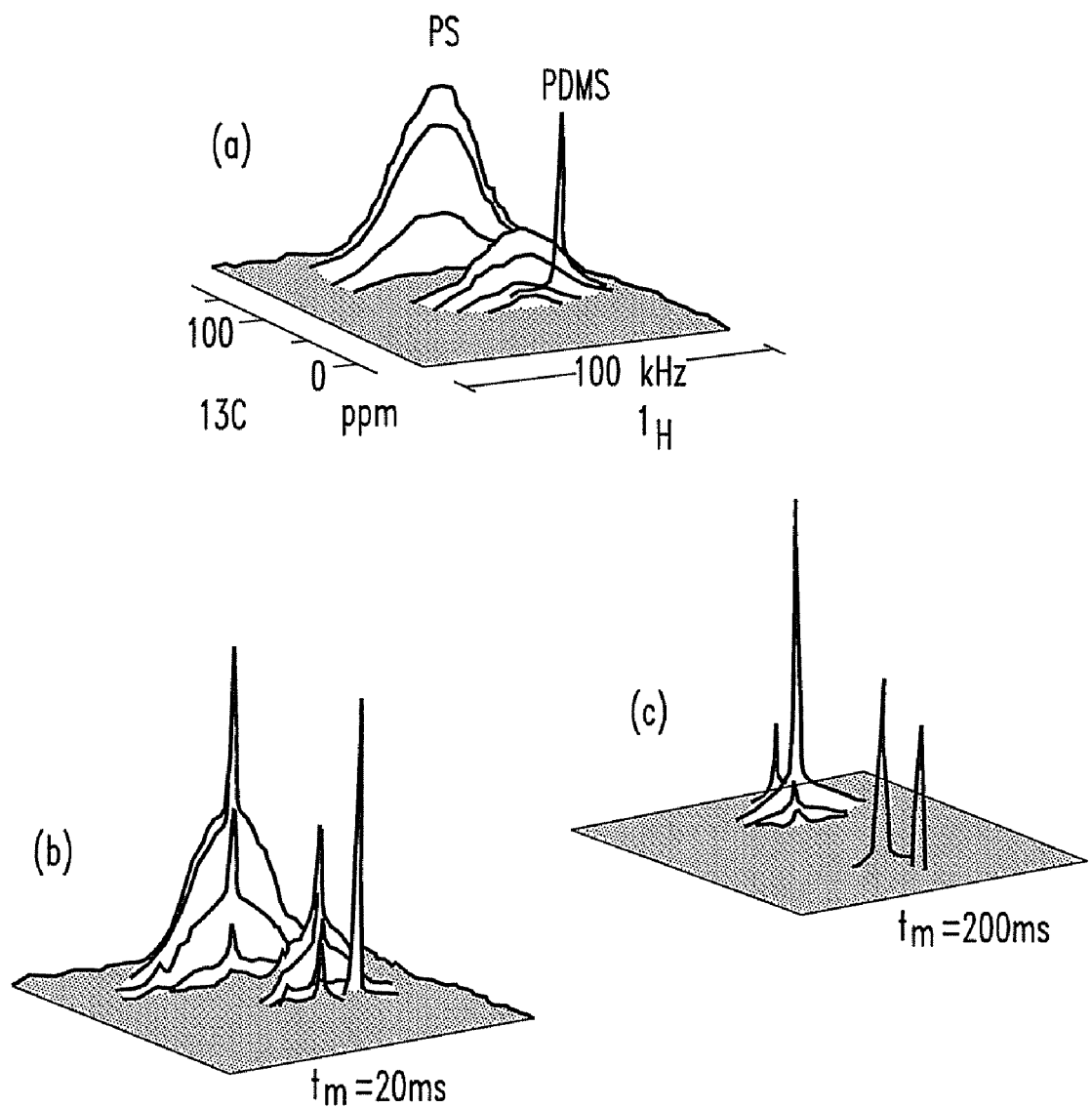
FIG. 6 illustrates examples of measurement in which magnetization transfer is effected while varying the time in which transverse magnetization relaxation times are measured.
Figure 7:
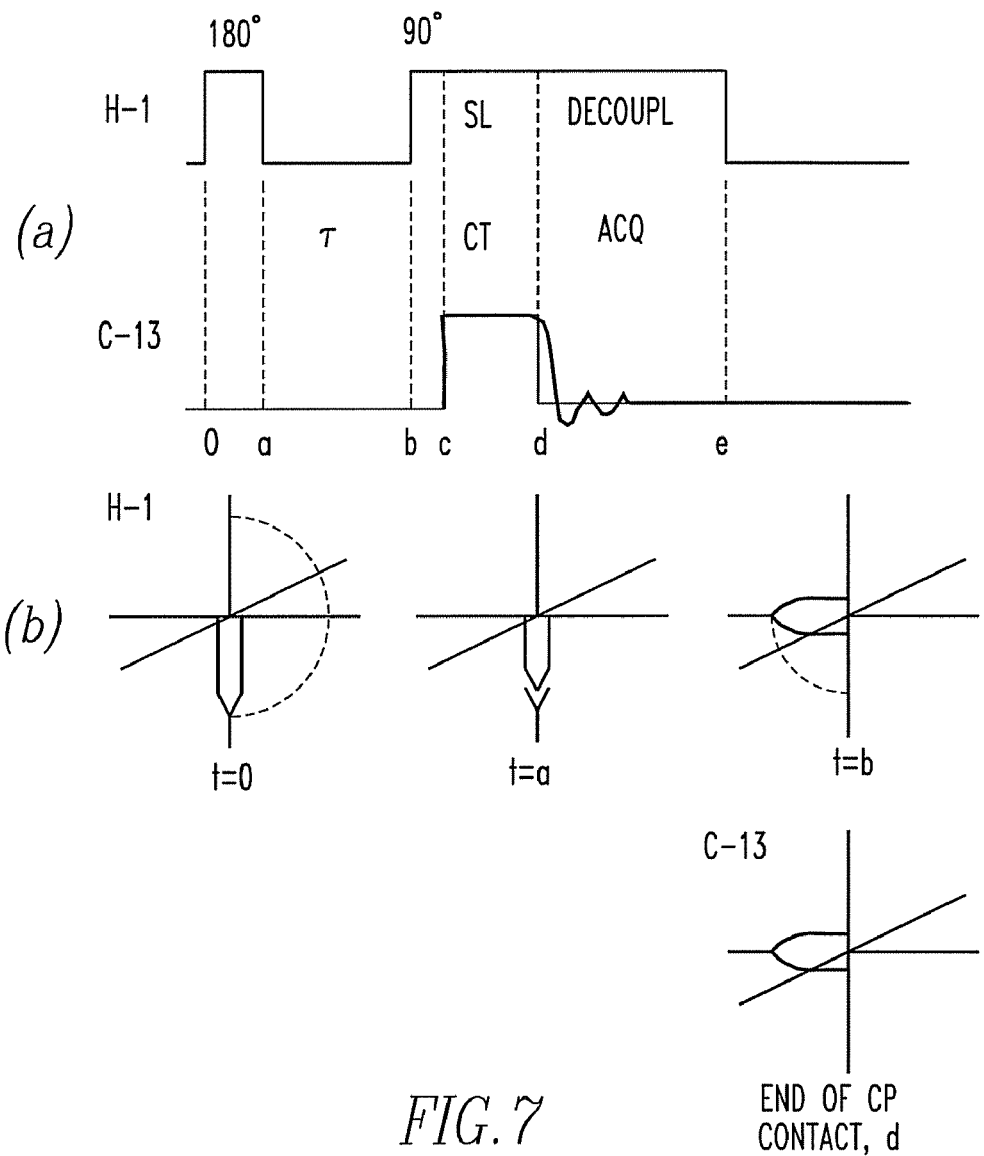
FIG. 7 illustrates an example of measurement in which magnetization transfer is effected after measurement of longitudinal magnetization relaxation times.
Figure 8:
FIG. 8 is a flowchart illustrating one example of an NMR measurement method associated with the present invention.

First, a method of separating peaks in a high-resolution NMR spectrum of spins I according to the longitudinal magnetization times of the spins I is described. To perform the separation, an NMR measurement illustrated in the flowchart of FIG. 8 is made. Because of this NMR measurement, the longitudinal magnetization relaxation times of the spins I can be measured through the spectrum of the spins I.

When an NMR spectrum of a mixture consisting of plural components is acquired, the high-resolution NMR spectrum of the spins I is a superimposition of NMR peaks of the various components. Peaks in the high-resolution NMR spectrum of the spins I obtained by this measurement can be classified according to the longitudinal magnetization relaxation times of the spins I.

That is, it is known that in normal NMR measurements, the strongest NMR signal is produced at thermal equilibrium, because the difference in the number of occupied states in a Boltzmann distribution between two energy levels is greatest at thermal equilibrium.

Accordingly, if longitudinal magnetization relaxation times are measured, spins I having shorter longitudinal magnetization relaxation times return to their thermal equilibrium in shorter times. As a result, the NMR spectral intensities of the spins I having shorter longitudinal magnetization relaxation time recover more quickly. Conversely, the spins I having longer longitudinal magnetization relaxation times return to their thermal equilibrium in longer times. As a result, the NMR spectral intensities of the spins I having longer longitudinal magnetization relaxation time recover more slowly.

Accordingly, an NMR spectrum of the spins I in which peaks are separated according to different longitudinal magnetization relaxation time can be obtained by measuring a high-resolution NMR spectrum of the spins I subsequently to measurement of the longitudinal magnetization relaxation times of the spins I and applying inverse Laplace transform to differences in recovery rate of NMR peak signal intensity originating from differences in longitudinal magnetization relaxation time among the spins I.

When the spins I are uniform in longitudinal magnetization relaxation time among each domain in a mixture, separation according to longitudinal magnetization relaxation time has the same meaning as separation according to each mixture component. That is, peaks in a high-resolution NMR spectrum can be separated according to each mixture component by separating the peaks in terms of longitudinal magnetization relaxation time.

Specific examples of the spins I include $^{1}H$ nuclei and $^{19}F$ nuclei in organic substances. In a compound including such nuclei, the longitudinal magnetization relaxation times of $^{1}H$ or $^{19}F$ nuclei are made uniform by homonuclear interactions. Observation is made under the conditions where the homonuclear interactions have been nullified. Consequently, a high-resolution NMR spectrum can be acquired.

Figure 9:
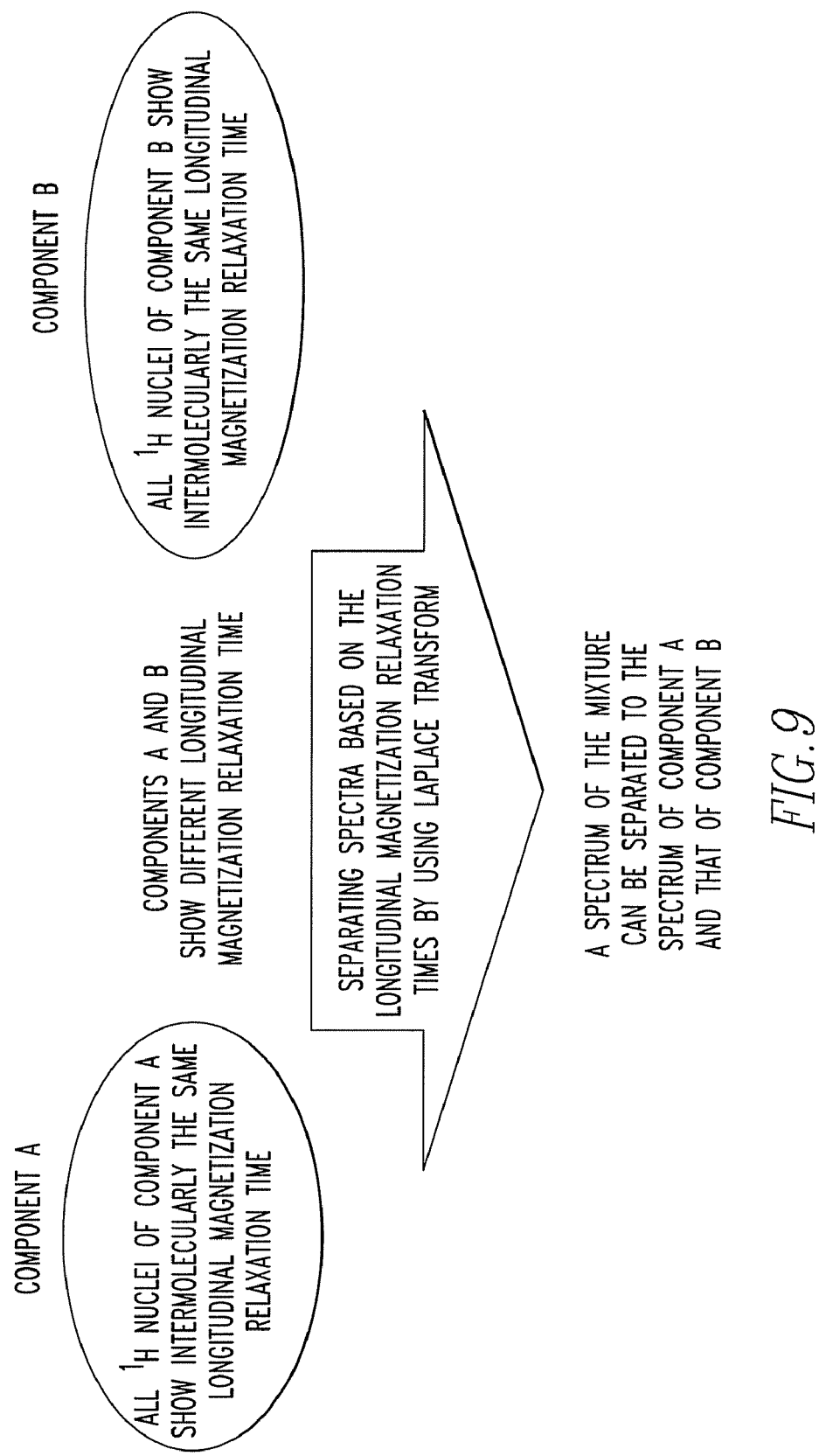
FIG. 9 is a chart illustrating another example of an NMR measurement method associated with the present invention.

As illustrated in FIG. 9, a high-resolution NMR spectrum of $^1$H nuclei or $^{19}$F nuclei in a mixture consisting of plural components can be observed as a high-resolution NMR spectrum of $^1$H nuclei or $^{19}$F nuclei of each component.

Figure 10:
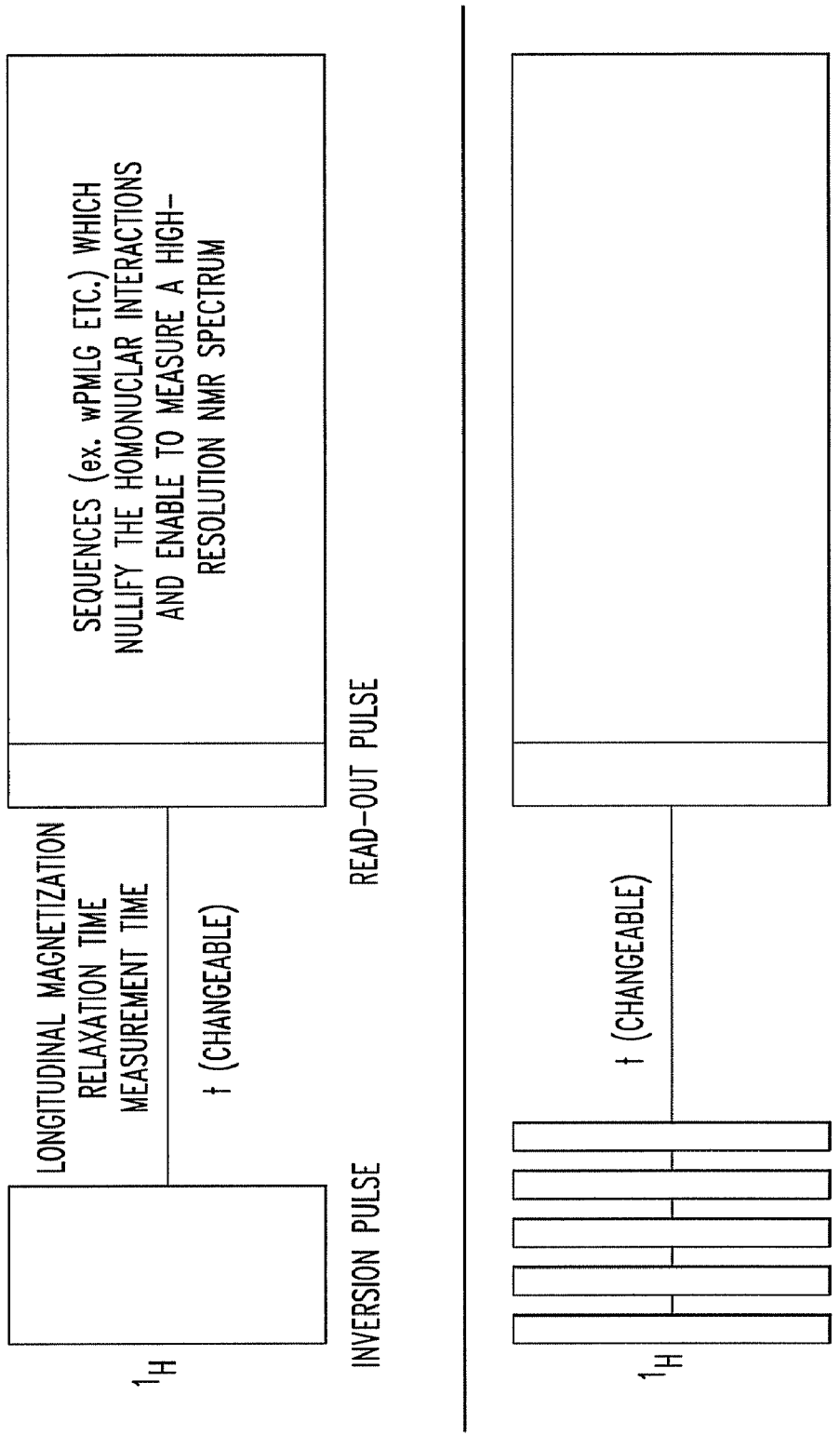
FIG. 10 shows time charts illustrating examples of an NMR measurement method associated with the present invention.

FIG. 10 schematically shows time charts of pulse sequences used in the present embodiment. The upper portion illustrates an example in which a method of inversion recovery is used to measure the longitudinal magnetization relaxation times of spins I. The lower portion illustrates an example in which a method of saturation recovery is used to measure the longitudinal magnetization relaxation times of spins I.

An inversion pulse sequence or saturation pulse sequence is applied to a mixture sample. After a lapse of a given waiting time t (longitudinal magnetization relaxation measurement time), a high-resolution NMR spectrum of spins I is acquired. High-resolution NMR spectra of the spins I are repeatedly acquired while varying the waiting time t gradually. Thus, it can be seen how the signal intensity of the high-resolution NMR spectrum of the spins I recovers dependently on the longitudinal magnetization relaxation time of the spins I. The method of measurement is described in detail below.

<Measurement of Longitudinal Magnetization Relaxation Time of Spins I>

In a case where spin-lattice relaxation time ($T_1$) of the spins I is used in separating spectral peaks: Where the simple expression "longitudinal magnetization relaxation times" is adopted, this case applies almost all the time:

The longitudinal magnetization relaxation time of the spins I is measured by a method of inversion recovery.

The longitudinal magnetization relaxation time of the spins I is measured by a method of saturation recovery.

In a case where the longitudinal magnetization relaxation time ($T_{1\rho}$) in the rotating frame of the spins I is used in separating peaks in a spectrum:

The longitudinal magnetization relaxation time ($T_{1\rho}$) in the rotating frame of the spins I is measured using spin locking.

In any measurement method, the magnitude of the magnetization of the spins I at the end of the measurement of the relaxation time varies dependently on the parameters used in measuring the relaxation time. This method of measurement is widely accepted in NMR spectroscopy.

<Measurement of High-resolution NMR Spectrum of Spins I>

A high-resolution NMR spectrum of the spins I can be accomplished by nullifying the aforementioned homonuclear interactions. This can be accomplished by appropriate irradiation with an RF magnetic field or high-speed rotation of the sample or by both.

<Inverse Laplace Transform>

Normally, relaxation times are analyzed by linear fitting. For this reason, it is sometimes difficult to analyze the relaxation times if there are plural components. Similar circumstances occur regarding analysis of diffusion coefficients. It has been somewhat cumbersome to analyze them.

However, with respect to diffusion coefficients, it has been shown using DOSY that the spectrum can be converted into a spectrum having peaks at the positions of the diffusion coefficients by applying inverse Laplace transform. The inverse Laplace transform can be similarly applied to analysis of relaxation times. A spectrum having peaks at the positions of relaxation times can be obtained.

Embodiment 2

A method of classifying high-resolution NMR spectra of spins S (in the following example, $^{13}$C nuclei) in terms of longitudinal magnetization relaxation time of the spins I (in most case, $^1$H) is next described. Examples of the spins S are various nuclear species which are other than $^1$H nuclei and include $^{13}$C, $^{15}$N, $^{29}$Si, and $^{31}$P nuclei capable of producing high-resolution NMR spectra.

To carry out this classification, NMR measurements illustrated in the flowchart of FIG. 11 are performed. That is, excited energies of the spins I are shifted to the spins S coupled to the spins I (magnetization transfer) while measuring the longitudinal magnetization relaxation times of the spins I. The longitudinal magnetization relaxation times of the spins I are measured throughout the high-resolution NMR spectrum of the spins S.

When an NMR spectrum of a mixture consisting of plural components is acquired, a high-resolution NMR spectrum of the spins S is a superimposition of NMR peaks of the individual components. NMR spectra of the spins S obtained by the present measurements can be classified according to longitudinal magnetization relaxation time of the spins I.

Specifically, in normal NMR measurements, it is known that the strongest NMR signal is produced at thermal equilibrium because the difference in the number of occupied states in a Boltzmann distribution between two energy levels is greatest at thermal equilibrium.

Accordingly, during measurement of longitudinal magnetization relaxation times, a spin I having a shorter longitudinal magnetization relaxation time returns to its thermal equilibrium state in a shorter time. As a result, the NMR spectral intensity of the spin S coupled to this spin I having a shorter longitudinal magnetization relaxation time is restored more quickly. Conversely, a spin I having a longer longitudinal magnetization relaxation time returns to its thermal equilibrium state in a longer time. As a result, the NMR spectral intensity of the spin S coupled to this spin I having a longer longitudinal magnetization relaxation time is restored more slowly.

Accordingly, if inverse Laplace transform is applied to the recovery rate of the NMR signal intensity of the spins S originating from the spin I, then a high-resolution NMR spectrum of the spins S in which peaks are separated according to different longitudinal magnetization relaxation time can be obtained.

When the spins I have a uniform longitudinal magnetization relaxation time within each component of a mixture, separation by the longitudinal magnetization relaxation times has the same meaning as separation by the mixture components. That is, the peaks in an NMR spectrum of the spins S can be separated according to the components by separating the peaks according to longitudinal magnetization relaxation time of the spins I.

Specific examples of the spins I include $^1$H nuclei and $^{19}$F nuclei in organic substances. In a compound including these nuclei, the longitudinal magnetization relaxation times of $^1$H or $^{19}$F nuclei are made uniform by homonuclear interactions.

For observation, the longitudinal magnetization relaxation times of $^1$H or $^{19}$F nuclei are measured and subsequently the magnetizations are moved to the spins S such as $^{13}$C nuclei. In consequence, the longitudinal magnetization relaxation times of $^1$H or $^{19}$F nuclei can be measured through a high-resolution NMR spectrum of $^{13}$C nuclei.

High-resolution NMR spectra as derived from $^{13}$C nuclei can be isolated based on the longitudinal magnetization relaxation times of $^1$H or $^{19}$F nuclei by applying inverse Laplace transform to the results of measurements.

As described so far, as illustrated in FIG. 12, a high-resolution NMR spectrum of $^{13}$C nuclei in a mixture consisting of plural components can be separated into high-resolution NMR spectra of $^{13}C$ nuclei in each individual component and observed.

Figure 13:
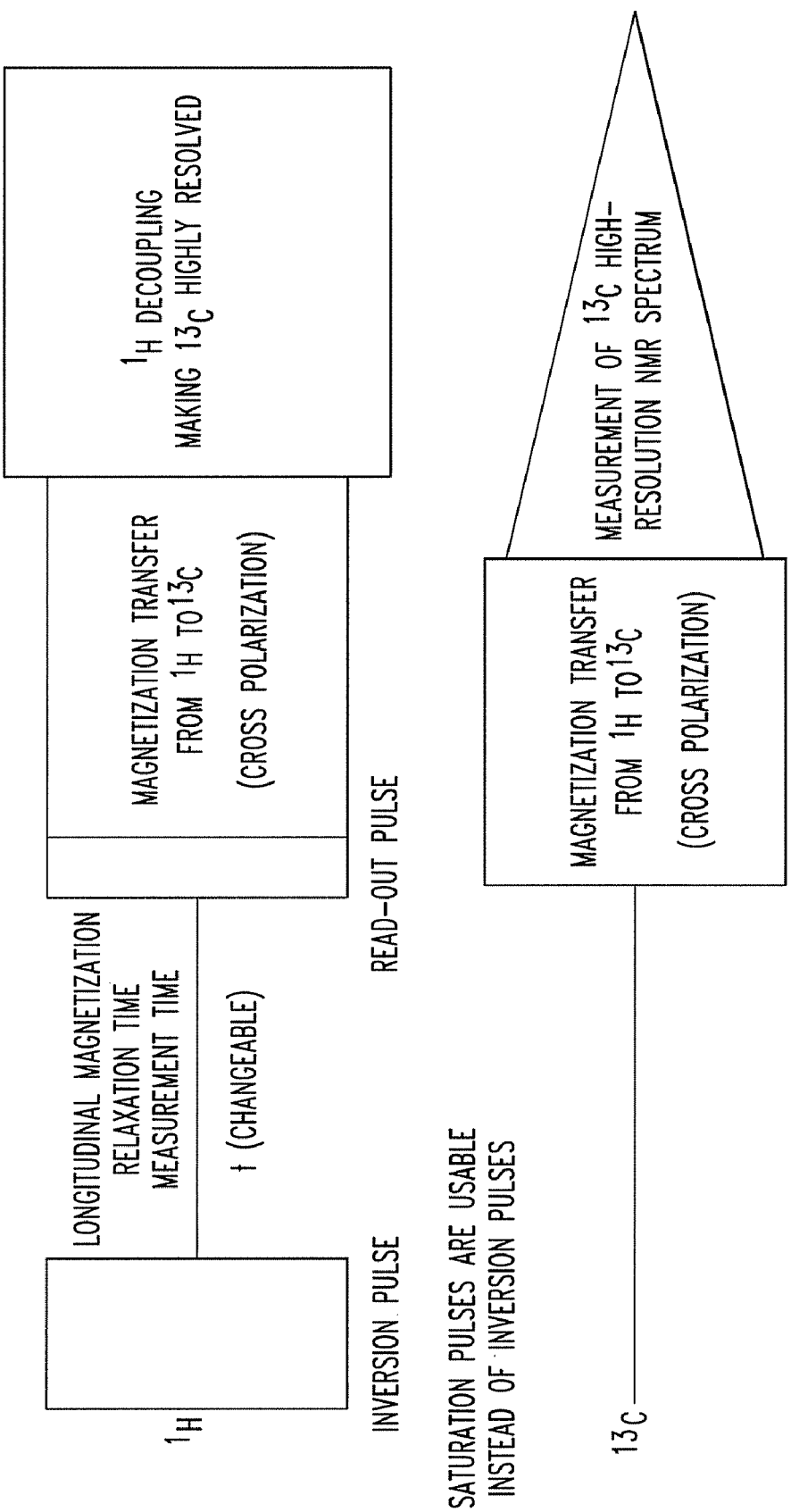
FIG. 13 illustrates still another example of an NMR measurement method associated with the present invention.

FIG. 13 is a schematic time chart of a pulse sequence used in the present embodiment. The upper portion illustrates an example in which a method of inversion recovery is used to measure the longitudinal magnetization relaxation times of spins I ($^1H$ nuclei). The lower portion illustrates an example in which a method of magnetization transfer is used to measure a high-resolution NMR spectrum of the spins S ($^{13}C$ nuclei) coupled to the spins I. A method of saturation recovery may also be used to measure the longitudinal magnetization relaxation times of the spins I ($^1H$ nuclei) in a manner not illustrated. $T_{1\rho}$ can be measured by using an excitation pulse sequence instead of an inversion pulse sequence and applying a spin-locking pulse during the period t in which the longitudinal magnetization relaxation times are measured.

An inversion pulse sequence on spin I (ex. $^1H$ nuclei) is applied to a mixture sample from a channel for $^1H$ nuclei. After a lapse of a given waiting time t during which the longitudinal magnetization relaxation times are measured, the magnetization of the spins I is moved to the spins S. After the magnetization transfer, a high-resolution NMR spectrum of the spins S is observed. During the observation, RF radiation on spin I is applied to the mixture sample to decouple the hetero nuclear dipolar interaction between spin S and spins I. Consequently, the signal arising from the coupling to the spins I is no longer broadened. Hence, a high-resolution NMR spectrum of the spins S can be acquired.

In actual measurements, high-resolution NMR spectra of the spins S are repetitively acquired while gradually varying the waiting time t in which longitudinal magnetization relaxation is induced. In this way, it is possible to observe how the signal intensity of the high-resolution NMR spectrum of the spins S recovers dependently on the longitudinal magnetization relaxation time of the spins I. Details of the method of measurements are as follows.

<Measurements of Longitudinal Magnetization Relaxation Times of Spins I>

In a case where spin-lattice relaxation time ($T_1$) of the spins I is used in separating spectral peaks: Where the simple expression "longitudinal magnetization relaxation times" is adopted, this case applies almost all the time:

The longitudinal magnetization relaxation time of the spins I is measured by a method of inversion recovery.

The longitudinal magnetization relaxation time of the spins I is measured by a method of saturation recovery.

In a case where the longitudinal magnetization relaxation time ($T_{1\rho}$) in the rotating frame of the spins I is used in separating peaks in a spectrum:

The longitudinal magnetization relaxation time in the rotating frame of the spins I is measured using spin locking.

If any measurement method is used, the magnitude of the magnetization of the spins I at the end of the measurement of the relaxation time varies dependently on the parameters used in measuring the relaxation time. This method of measurement is widely accepted in NMR spectroscopy.

<Magnetization Transfer from Spins I to Spins S>

The magnetization of the spins I remaining at the end of the measurement of the longitudinal magnetization relaxation times of the spins I is shifted to the spins S. This technique is known as heteronuclear magnetization transfer and widely accepted in NMR measurements. Because of this magnetization transfer, the magnitude of the magnetization of the spins I modulated by a relaxation time parameter is observed as the magnitude of the magnetization of the spins S.

That is, the relaxation times of the spins I can be indirectly analyzed by analyzing variations in the magnitude of the magnetization of the spins S.

<Measurement of High-resolution NMR Spectra of Spins S>

The time evolution of the magnetization shifted from the spins I to the spins S by magnetization transfer is observed as a high-resolution NMR spectrum of the spins S.

<Inverse Laplace Transform>

Normally, relaxation times are analyzed by linear fitting. For this reason, it is sometimes difficult to analyze the relaxation times if there are plural components. Similar circumstances occur regarding analysis of diffusion coefficients. It has been somewhat cumbersome to analyze them.

However, with respect to diffusion coefficients, it has been shown using DOSY that the spectrum can be converted into a spectrum having peaks at the positions of the diffusion coefficients by applying inverse Laplace transform. The inverse Laplace transform can be similarly applied to analysis of relaxation times. A spectrum having peaks at the positions of relaxation times can be obtained.

Embodiment 3

The point of the present invention is to measure the longitudinal magnetization relaxation time of the spins I while they are uniform in longitudinal magnetization relaxation time within each individual component due to spin diffusion, thus acquiring a high-resolution NMR spectrum.

In Embodiments 1-2, measurements were performed under the condition where spins I were present at high density and uniform longitudinal magnetization relaxation time was intrinsically achieved by spin diffusion. On the other hand, it is reported that spin diffusion can be promoted artificially even if spins I are present at low density (such as DARR (dipolar assisted rotational resonance) producing a $^{13}C$-$^{13}C$ distance correlation).

Accordingly, it is conceivable that spin diffusion could be promoted artificially during measurement of longitudinal magnetization relaxation times of the spins I to achieve a uniform longitudinal magnetization relaxation time artificially and that a high-resolution NMR spectrum of the spins I could then be acquired.

Furthermore, it is conceivable that spin diffusion could be promoted artificially during measurement of longitudinal magnetization relaxation times of the spins I to achieve a uniform relaxation time artificially and that magnetization transfer could then be effected from the spins I to the spins S and a high-resolution NMR spectrum of the spins S be acquired.

Embodiment 4

In Embodiments 1-3 described above, one-dimensional spectra are separated. Multidimensional NMR spectra can also be separated by using multidimensional NMR spectroscopy in accepting NMR signals.

In brief, the present invention yields the following advantages.

(1) NMR spectra of a mixture consisting of plural components can be acquired separately for each individual component. Therefore, it is not necessary to refine the mixture. Measurements can be made separately for each individual component.

(2) Inverse Laplace transform is used for analysis of relaxation times. This dispenses with complex operations such as linear fitting operations. Where plural components are overlapped, it is easy to analyze the relaxation times.

(3) Because it is not necessary to refine mixtures, a measurement can be performed on a reaction product being synthesized while by-products and reaction intermediates are contained in the reaction product. This is useful for confirmation of the reaction.

(4) Where different domains are made of different crystalline systems if the domains consist of identical molecules, the domains show different relaxation times. This fact can be employed for analysis of substances having crystal polymorphism (which have attracted attention in the pharmaceutical industry).

(5) NMR spectra, respectively, of different components of a sample containing both crystalline and amorphous portions can be separated and observed.

EXAMPLE OF MEASUREMENT

The results of actual measurements on a mixture of santonin and cholesterol are shown. The spin-lattice relaxation time (longitudinal magnetization relaxation time) of $^1H$ was used to separate the NMR peaks of the mixture. Similarly to normal organic substances, satonin and cholesterol showed uniform $^1H$ magnetization relaxation times within their respective domains. However, $^1H$ longitudinal magnetization relaxation time was different between santonin and cholesterol. Based on this premise, spectra were separated.

Inverse Laplace transform was used to analyze relaxation times. $^{13}C$ NMR was used to obtain high-resolution NMR spectra. The measurements were carried out by measuring the $^1H$ longitudinal magnetization relaxation times followed by magnetization transfer from $^1H$ to $^{13}C$, and giving rise to a high-resolution $^{13}C$ NMR spectrum.

As shown in "$^{13}C$ NMR spectrum of mixture" of FIG. 12, a normal $^{13}C$ NMR spectrum is a superimposition of a $^{13}C$ NMR spectrum of santonin and a $^{13}C$ NMR spectrum of cholesterol.

Figure 14:
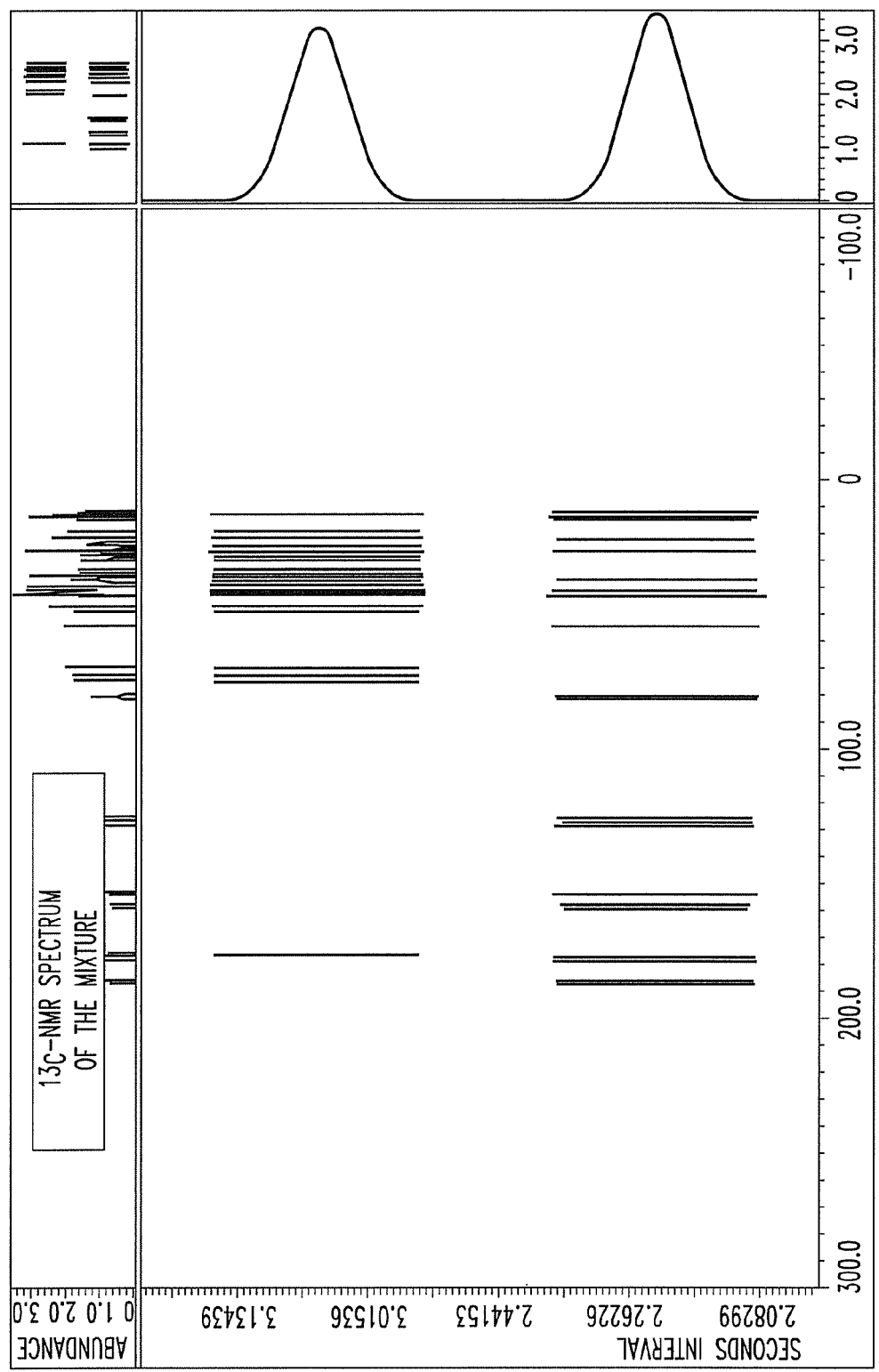
FIG. 14 is a chart showing the results of a measurement on a mixture sample including santonin and cholesterol, the measurement being performed by a method according to the present invention.

The results of an analysis of longitudinal magnetization relaxation times are shown in the lower part of FIG. 14. As a result of use of inverse Laplace transform, a spectrum having peaks at the positions of longitudinal magnetization relaxation times appears. The vertical axis indicates relaxation time. It can be seen that the spectral peaks are resolved into two sets of peaks. One (lower part of the spectrum) arises from santonin, while the other (upper part) arises from cholesterol.

Figure 15:
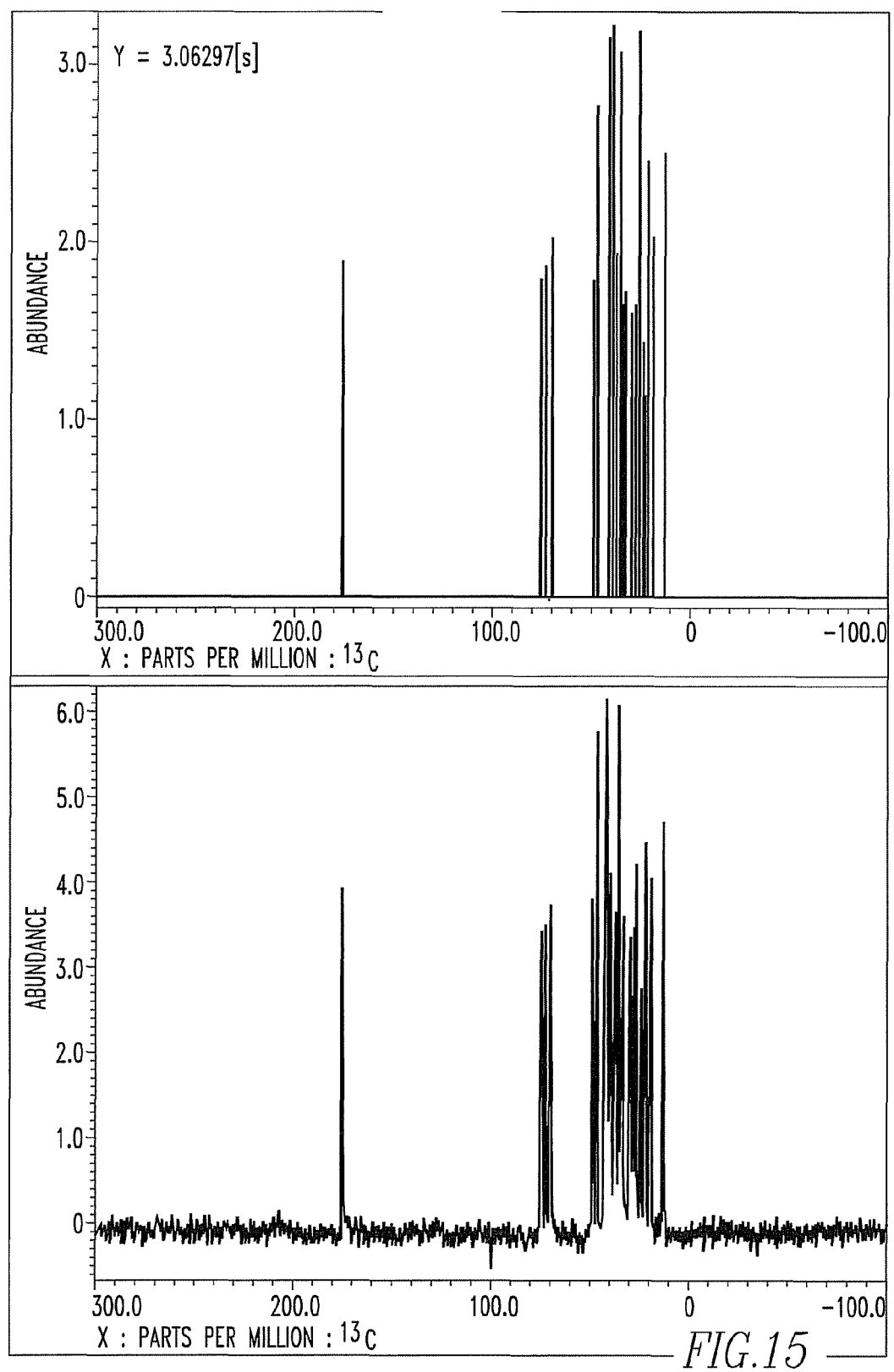
FIG. 15 shows $^{13}C$ NMR spectra of cholesterol isolated from the mixture sample by the present invention and $^{13}C$ NMR spectra of pure cholesterol.
Figure 16:
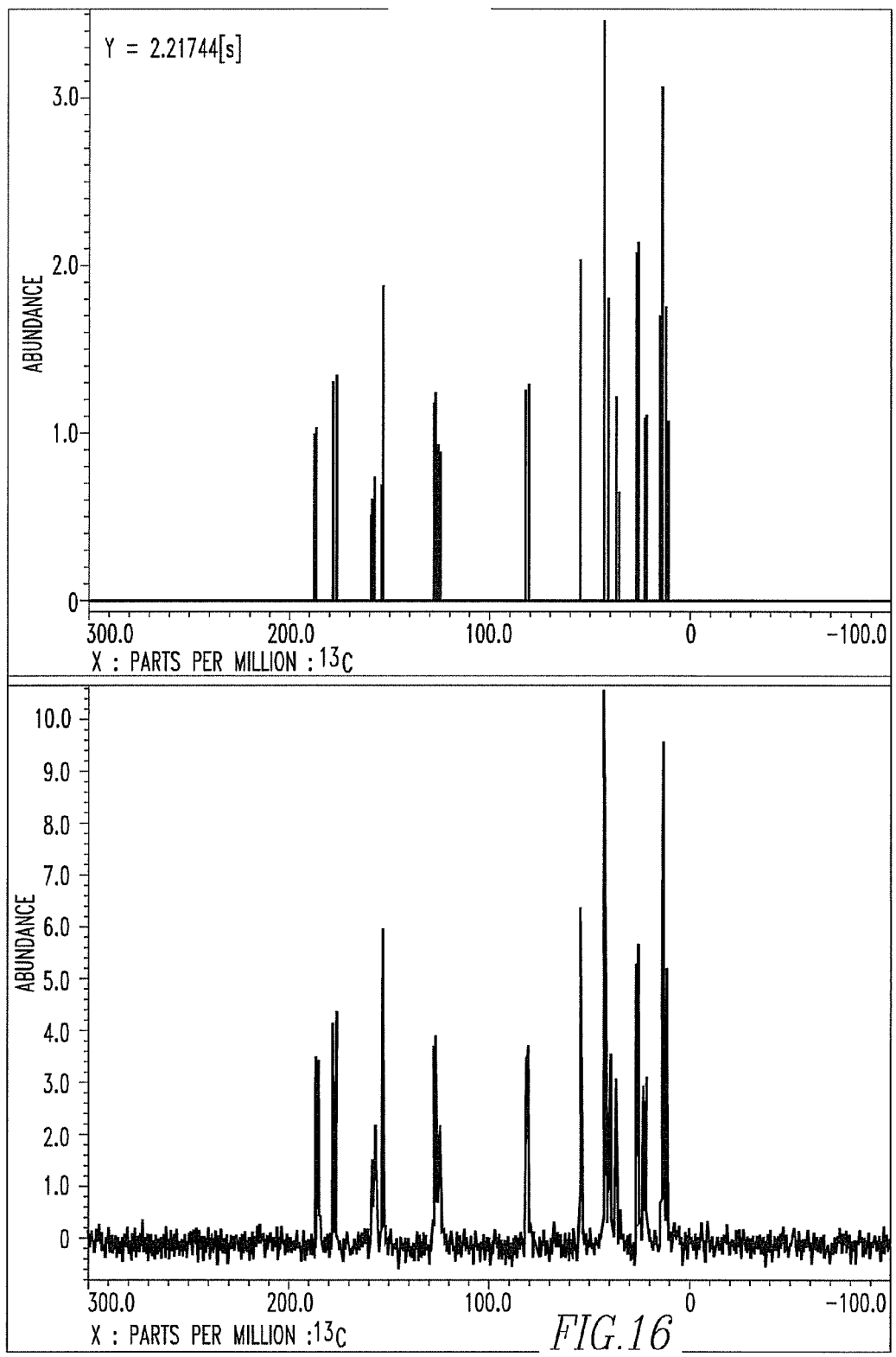
FIG. 16 shows $^{13}C$ NMR spectra of santonin isolated from the mixture sample by the present invention and $^{13}C$ NMR spectra of pure santonin.

A spectral slice was taken at each longitudinal magnetization relaxation time. The results are shown in FIGS. 15 and 16. The upper part of FIG. 15 is a spectral slice taken at a longitudinal magnetization relaxation time of 3.06 seconds. The lower part of FIG. 15 shows a $^{13}C$ NMR spectrum obtained from a sample consisting only of pure cholesterol. In spite of the fact that the upper part of FIG. 15 is a spectral slice derived from a mixture, it can be seen that only NMR signals of cholesterol are observed.

The upper part of FIG. 16 is a spectral slice taken at a longitudinal magnetization relaxation time of 2.2 seconds. The lower part of FIG. 16 shows a $^{13}C$ NMR spectrum obtained from only pure santonin. The upper part of FIG. 16 is a spectral slice obtained from a mixture but it can be seen that only NMR signals from santonin are observed.

As described so far, it has been shown that an NMR spectrum is resolved into NMR spectra or NMR spectral slices corresponding to different components by applying the technique of the present invention to a mixture consisting of the plural components without refining the mixture.

The present invention can find use in a wide ranges of NMR measurements of mixtures.

Having thus described my invention with the detail and particularity required by the Patent Laws, what is desired protected by Letters Patent is set forth in the following claims.

The invention claimed is:

1. An NMR measurement method for obtaining NMR spectra, respectively, of plural components of a sample when the nuclear spins in the components have a uniform longitudinal magnetization relaxation time in each individual domain of the sample due to spin diffusion, said method comprising the steps of:
  irradiating a pulse sequence to the sample in order to measure the above-described uniform longitudinal magnetization relaxation time of nuclei;
  after a lapse of a given period of time t, acquiring a high-resolution NMR spectrum by nullifying the spin diffusion of the nuclei having the uniform longitudinal magnetization relaxation time;
  repeating the irradiating step and the NMR spectrum-acquiring step while varying the period of time t to obtain plural high-resolution NMR spectra; and
  classifying the high-resolution NMR spectra according to value of longitudinal magnetization relaxation time by inverse Laplace transform, based on differences in recovery rate of NMR signal intensity that recovers dependently on longitudinal magnetization relaxation time.

2. An NMR measurement method as set forth in claim 1, wherein said longitudinal magnetization relaxation times are measured by an inversion recovery method.

3. An NMR measurement method as set forth in claim 1, wherein said longitudinal magnetization relaxation times are measured by a saturation recovery method.

4. An NMR measurement method as set forth in claim 1, wherein the nuclei having said longitudinal magnetization relaxation times are in a rotating frame and the longitudinal magnetization relaxation times are measured by a spin locking method.

5. An NMR measurement method as set forth in claim 1, wherein said spin diffusion is nullified by RF irradiation for nullifying homonuclear interactions or high-speed rotation of the sample or by both.

6. An NMR measurement method as set forth in claim 1, wherein the nuclei having said uniform longitudinal magnetization relaxation time are $^1H$ nuclei or $^{19}F$ nuclei.

7. An NMR measurement method for obtaining NMR spectra, respectively, of plural components of a sample when nuclear spins (the first spins) have a uniform longitudinal magnetization relaxation time in each individual domain of the sample due to spin diffusion, said method comprising the steps of:
  irradiating a pulse sequence to the sample in order to measure said uniform longitudinal magnetization relaxation time of the first nuclei;
  after a lapse of a given period of time t, transferring magnetization from the first nuclei to second nuclei which receive energies of the first nuclei and give a high-resolution NMR spectrum, and acquiring a high-resolution NMR spectrum of the second nuclei;
  repeating the irradiating step and the acquiring step to acquire plural high-resolution NMR spectra of the second nuclei while varying the period of time t; and
  classifying the high-resolution NMR spectra of the second nuclei according to value of longitudinal magnetization relaxation time by inverse Laplace transform, based on differences in recovery rate of NMR signal intensity that recovers dependently on longitudinal magnetization relaxation time.

8. An NMR measurement method as set forth in claim 7, wherein said longitudinal magnetization relaxation times are measured by an inversion recovery method.

9. An NMR measurement method as set forth in claim 7, wherein said longitudinal magnetization relaxation times are measured by a saturation recovery method.

10. An NMR measurement method as set forth in claim 7, wherein the nuclei having said longitudinal magnetization relaxation times are in a rotating frame and the longitudinal magnetization relaxation times are measured by a spin locking method.

11. An NMR measurement method as set forth in claim 7, wherein said first nuclei are $^1$H nuclei or $^{19}$F nuclei.

12. An NMR measurement method as set forth in claim 7, wherein said second nuclei are other than $^1$H nuclei and can give rise to high-resolution NMR spectra.

13. An NMR measurement method as set forth in claim 12, wherein said second nuclei are $^{13}$C nuclei, $^{15}$N nuclei, $^{29}$S nuclei, or $^{31}$P nuclei.

\* \* \* \* \*